(12) United States Patent
Freeman et al.

(10) Patent No.: US 12,247,969 B2
(45) Date of Patent: Mar. 11, 2025

(54) METHOD AND SYSTEM FOR CHARACTERISING THE SOIL MOISTURE CHARACTERISTICS OF MANAGEMENT ZONES IN BOTH TIME AND SPACE, SPECIFIC TO ZONE-BASED MANAGEMENT FOR VARIABLE RATE CROP INPUTS

(71) Applicant: Croptimistic Technology Inc., Naicam (CA)

(72) Inventors: Jonathan Freeman, Naicam (CA); Corwyn Willness, Naicam (CA); Derek Rude, Naicam (CA)

(73) Assignee: Croptimistic Technology Inc., Naicam (CA)

( * ) Notice: Subject to any disclaimer, the term of this patent is extended or adjusted under 35 U.S.C. 154(b) by 204 days.

(21) Appl. No.: 18/170,989

(22) Filed: Feb. 17, 2023

(65) Prior Publication Data

US 2023/0349880 A1  Nov. 2, 2023

Related U.S. Application Data

(60) Provisional application No. 63/318,557, filed on Mar. 10, 2022.

(51) Int. Cl.
  *G01N 33/24* (2006.01)
  *G01N 27/04* (2006.01)

(52) U.S. Cl.
  CPC .......... *G01N 33/246* (2013.01); *G01N 27/04* (2013.01); *G01N 33/245* (2024.05)

(58) Field of Classification Search
  CPC ..... G01N 33/246; G01N 27/04; G01N 33/245
  See application file for complete search history.

(56) References Cited

U.S. PATENT DOCUMENTS

| | | | |
|---|---|---|---|
| 11,035,838 B2 * | 6/2021 | Willness | G01C 9/06 |
| 2013/0209172 A1 * | 8/2013 | Smucker | A01G 29/00 |
| | | | 405/38 |
| 2015/0305227 A1 * | 10/2015 | Zemenchik | A01C 7/102 |
| | | | 172/776 |
| 2017/0343485 A1 * | 11/2017 | Garrison | G01S 13/003 |
| 2019/0230875 A1 * | 8/2019 | Mewes | A01B 79/005 |

* cited by examiner

*Primary Examiner* — Alvaro E Fortich
(74) *Attorney, Agent, or Firm* — Michael R. Williams; Ryan W Dupuis; Ade & Company Inc.

(57) ABSTRACT

A method and system for a hydrological process that describes and characterises either statically or temporally, soil moisture variability within agricultural fields, specific to zone-based field recommendations. Surface and subsurface hydrological processes are combined with soil physical properties, electrical conductivity (EC), topography, soil moisture sensors and climate parameters from weather stations, to produce a zone-based soil moisture balance. This process facilitates in-season optimization of crop inputs such as water from irrigation, seed, nutrients, herbicides, or pesticides based on the soil moisture conditions throughout a field.

20 Claims, 13 Drawing Sheets

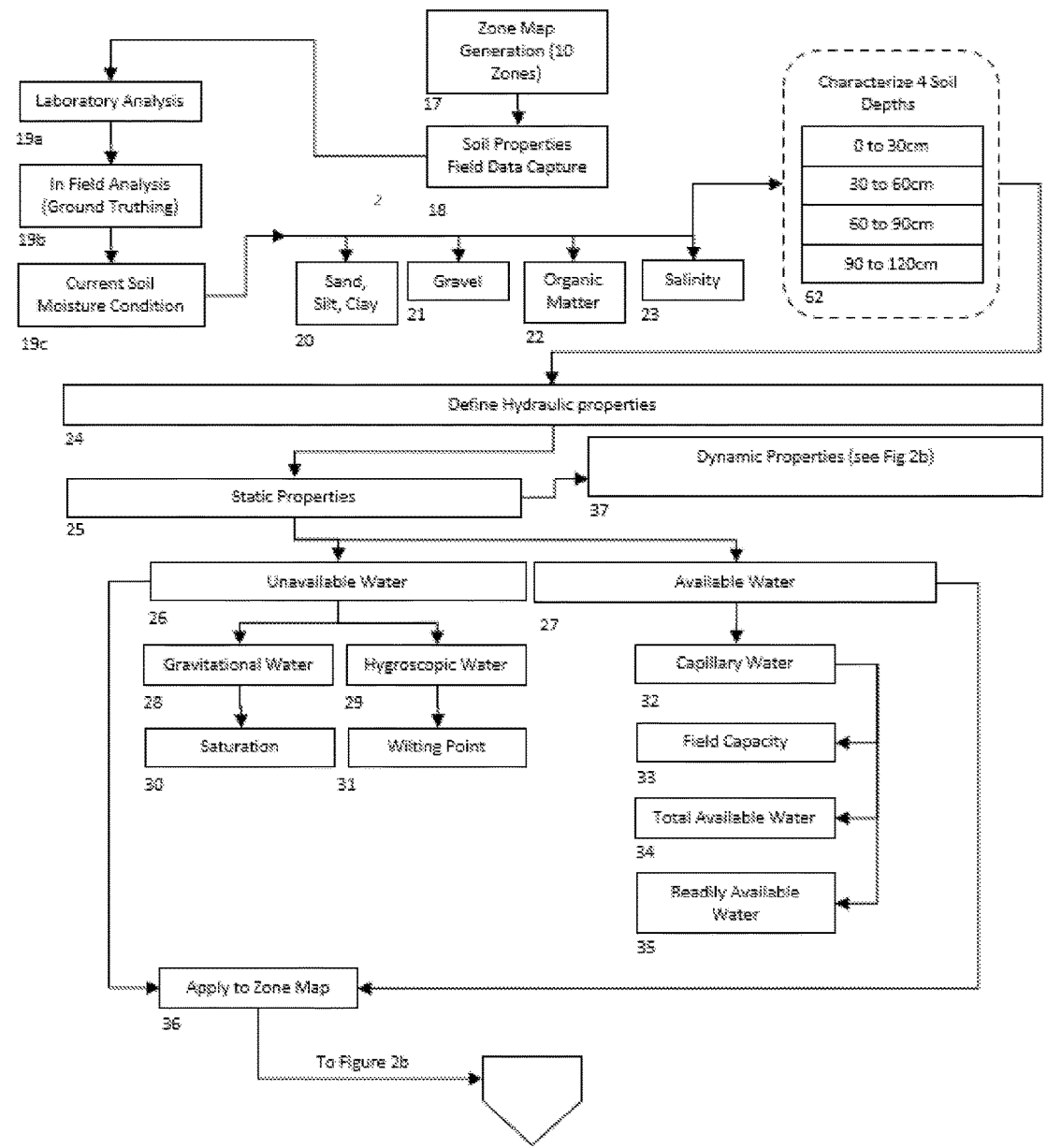
FIG. 2.1

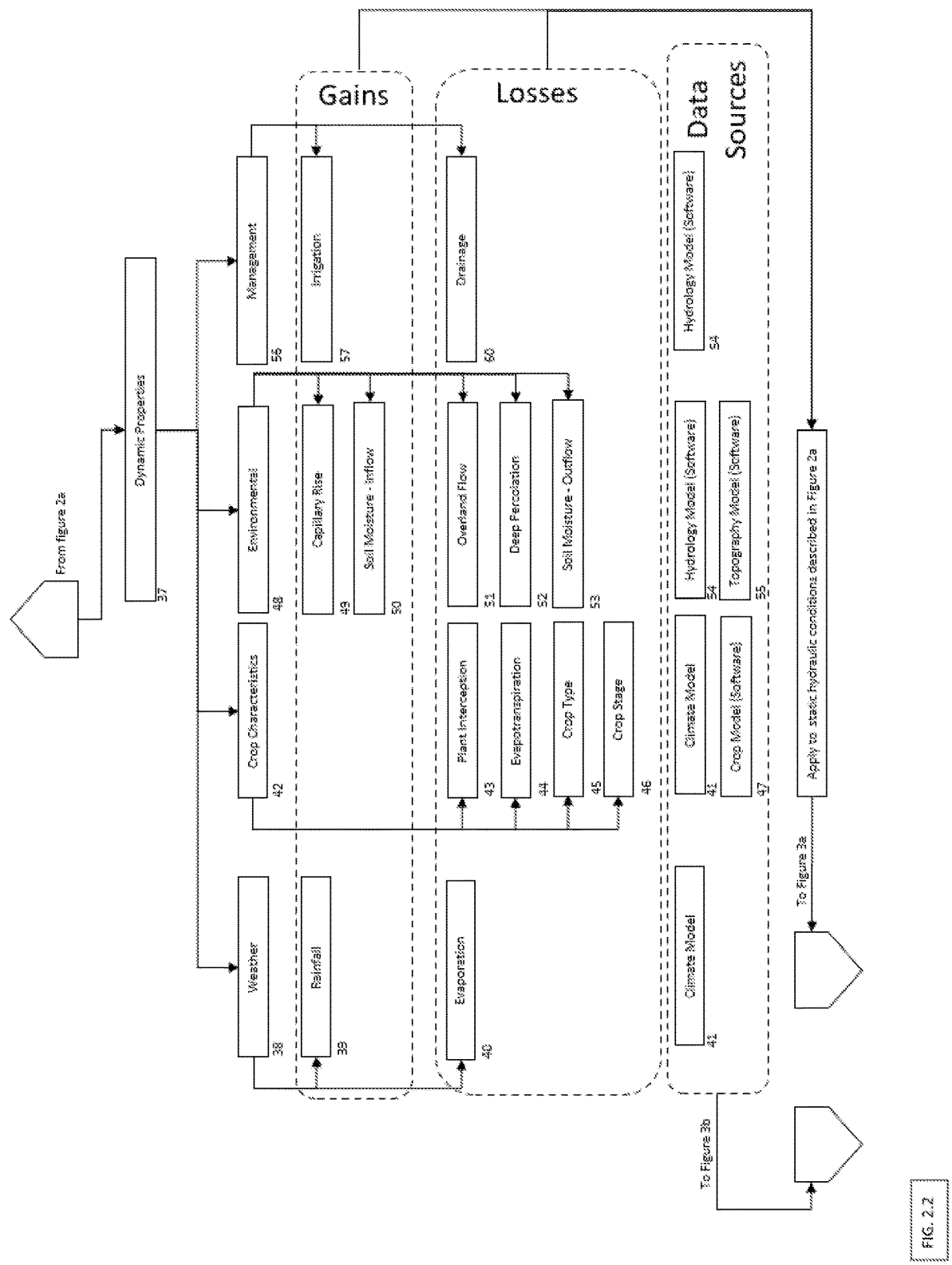
FIG. 2.2

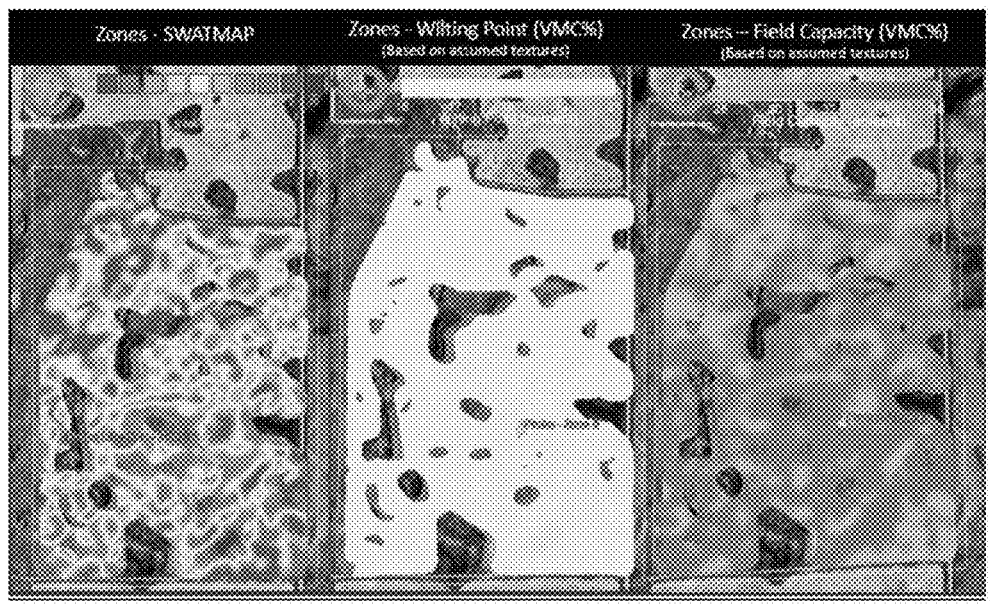
FIG. 2.3
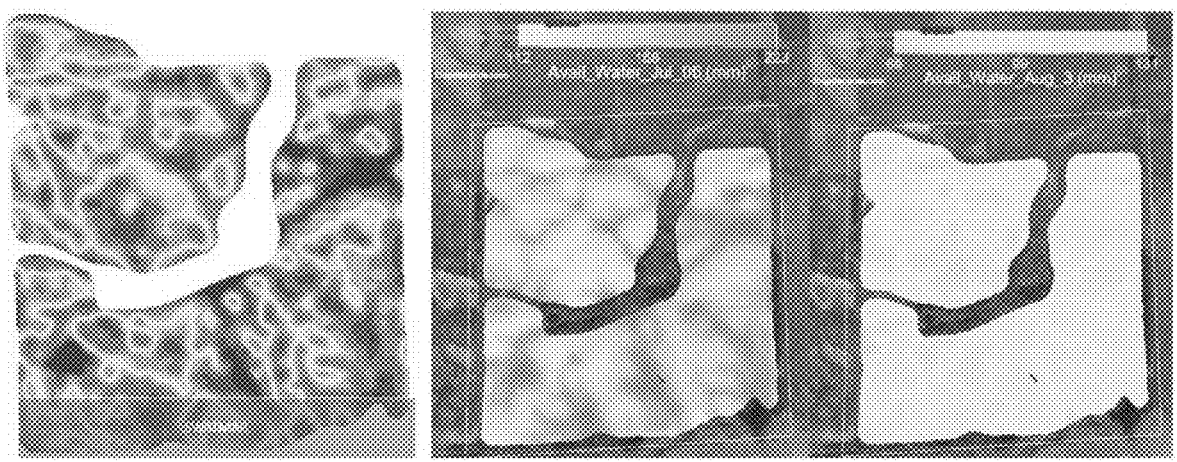
FIG. 2.4

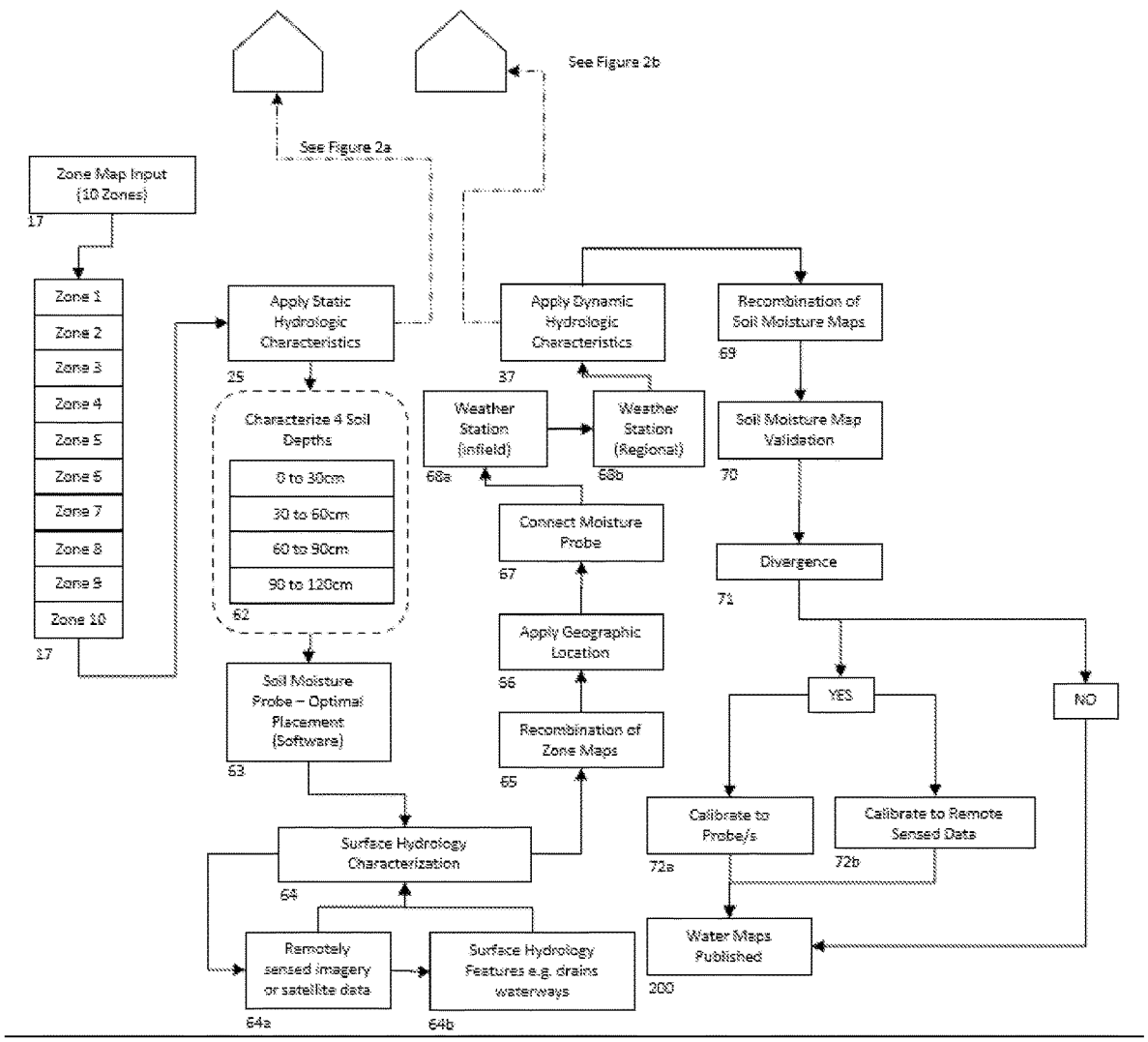
FIG. 3.1

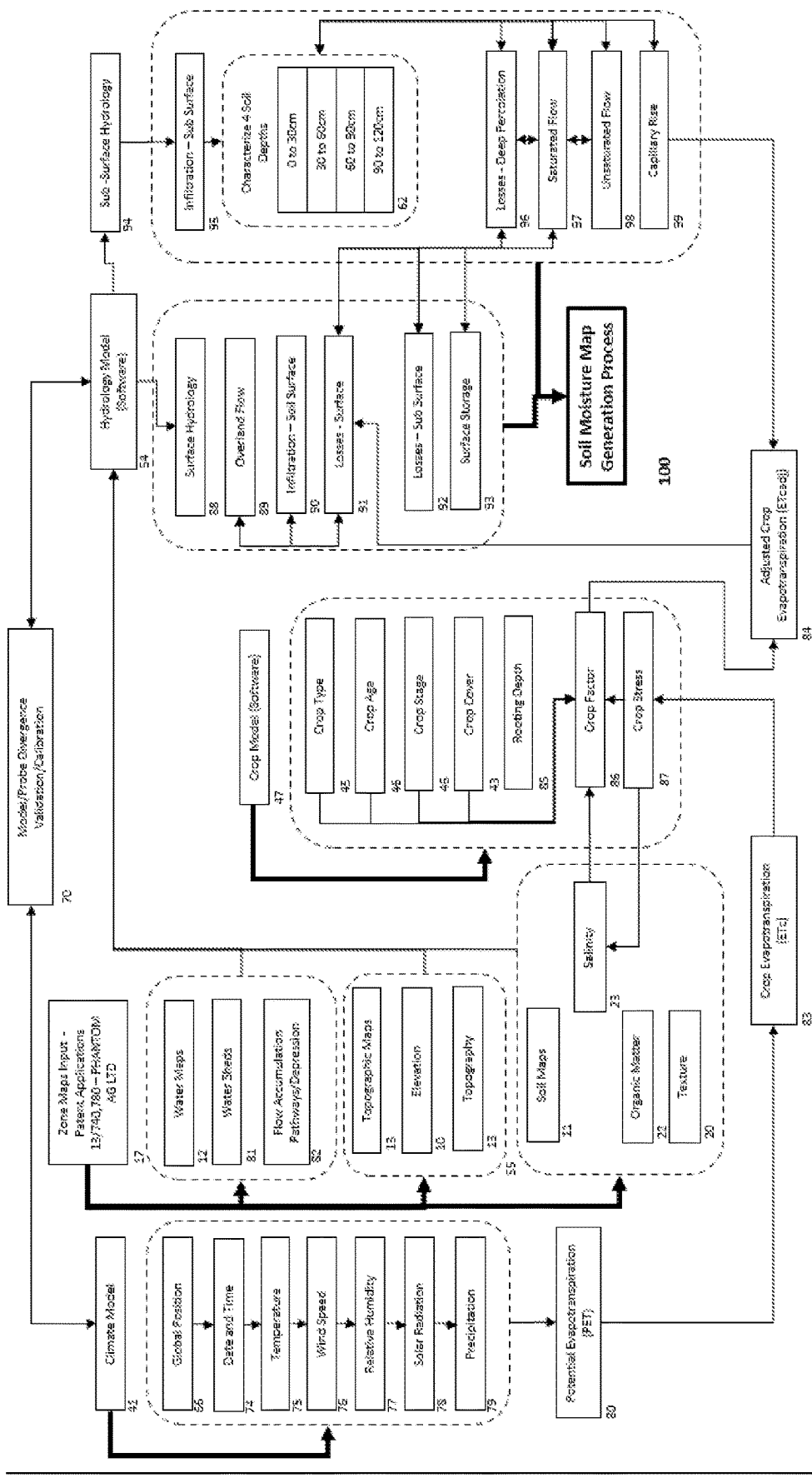
FIG. 3.2

Default Grid is:

Filename: ZoneMaps\cwm1Croppers 30EMC 50LMF

FieldID: a43e0b6a-af2e-4ac1-82e7-6cc089891ba

Zone Map:

0 to 254 (370, 406)

View

ZoneMaps\cwm1Croppers 30EMC 50LMF SW

Elevation Grid:

1845.9 to 1908.8 Feet (370, 406)

View

MapsData\Elevation.grid

FIG. 4.1

Zone Map Depth:

12 Inches Depth

☐ Generate normal depth grid.
☐ Generate rooting depth grid.
☒ Generate total depth grid.

Dynamic Grid Date:

Farming Season Start: 5/16/2021 12:00:00 AM

Change the season Season in the field properties tab.

Map Value At: 12/1/2021  15    Hour: 0  (00-24)

FIG. 4.2

Zone Classification

| Zone | 2 - 96% Sand: REQUIRED | 2 - 96% Clay: REQUIRED | 0 - 8% Org Matter: REQUIRED | 0 - 65% Gravels: Optional | 0.9 - 1.3 Density Factor: Optional | 0-20 dS/m Salinity: Optional |
|---|---|---|---|---|---|---|
| 1 | 71 | 7 | 2.7 | 0 | 1 | 0 |
| 2 | 67 | 7 | 2.3 | 0 | 1 | 0 |
| 3 | 66 | 7.1 | 1.9 | 0 | 1 | 0 |
| 4 | 66.6 | 9 | 2.5 | 0 | 1 | 0 |
| 5 | 61.6 | 10.9 | 3 | 0 | 1 | 0 |
| 6 | 56.3 | 12.6 | 2.8 | 0 | 1 | 0 |
| 7 | 50.9 | 14.2 | 2.5 | 0 | 1 | 0 |
| 8 | 51.6 | 14 | 2.9 | 0 | 1 | 0 |
| 9 | 51 | 14 | 3.2 | 0 | 1 | 0 |
| 10 | 50 | 13.6 | 3.6 | 0 | 1 | 0 |

FIG. 4.3

Zone Classification:

| Zone | 2-96% Sand REQUIRED | 2-96% Clay REQUIRED | 0-8% Org Matter REQUIRED | 0-65% Gravels Optional | 0.9-1.3 Density Factor Optional | 0-20 dS/m Salinity Optional | Starting Moisture (mm) | Soil Classification: Calculated | Calculated Value Calculated | Available Water Calculated | Field Capacity Calculated | Wilt Point Calculated | Starting Moisture (frac) |
|---|---|---|---|---|---|---|---|---|---|---|---|---|---|
| 1 | 71 | 7 | 2.7 | 0 | 1 | 0 | 40 | Sandy Loam | Choose Grid | 0.08 cm/cm | 0.15 %Vol | 0.07 %Vol | 0.1333 |
| 2 | 67 | 7 | 2.3 | 0 | 1 | 0 | 41 | Sandy Loam | Choose Grid | 0.10 cm/cm | 0.16 %Vol | 0.06 %Vol | 0.1367 |
| 3 | 66 | 7.1 | 1.9 | 0 | 1 | 0 | 42 | Sandy Loam | Choose Grid | 0.10 cm/cm | 0.15 %Vol | 0.06 %Vol | 0.14 |
| 4 | 65.6 | 9 | 2.5 | 0 | 1 | 0 | 55 | Sandy Loam | Choose Grid | 0.10 cm/cm | 0.17 %Vol | 0.07 %Vol | 0.1833 |
| 5 | 61.6 | 10.9 | 3 | 0 | 1 | 0 | 55 | Sandy Loam | Choose Grid | 0.11 cm/cm | 0.20 %Vol | 0.09 %Vol | 0.1833 |
| 6 | 58.3 | 12.6 | 2.8 | 0 | 1 | 0 | 56 | Sandy Loam | Choose Grid | 0.12 cm/cm | 0.22 %Vol | 0.10 %Vol | 0.1867 |
| 7 | 50.9 | 14.2 | 3.5 | 0 | 1 | 0 | 57 | Loam | Choose Grid | 0.13 cm/cm | 0.23 %Vol | 0.10 %Vol | 0.19 |
| 8 | 51.6 | 13 | 2.9 | 0 | 1 | 0 | 58 | Loam | Choose Grid | 0.11 cm/cm | 0.23 %Vol | 0.11 %Vol | 0.1933 |
| 9 | 51 | 14 | 3.2 | 0 | 1 | 0 | 59 | Loam | Choose Grid | 0.13 cm/cm | 0.24 %Vol | 0.11 %Vol | 0.1967 |
| 10 | 50 | 13.6 | 3.6 | 0 | 1 | 0 | 60 | Loam | Choose Grid | 0.13 cm/cm | 0.24 %Vol | 0.11 %Vol | 0.2 |

FIG. 4.4.

CANSIS Data:

| Component Number | Percentage of Occurrence | Soil Name | Sand Percentage | Silt Percentage | Clay Percentage | Organic Matter | Bulk Density | Declared Texture |
|---|---|---|---|---|---|---|---|---|
| 1 | 23 | OXBOW CA.BLC | 47 | 32 | 21 | 2.8 | 0 | Loam |
| 2 | 20 | YORKTON CA.BLC | 46 | 34 | 20 | 3.8 | 0 | Loam |
| 3 | 19 | OXBOW O.BLC | 47 | 32 | 21 | 3.2 | 0 | Loam |
| 4 | 12 | OXBOW CA.BLC | 47 | 32 | 21 | 2.8 | 0 | UNKNOWN |
| 5 | 11 | GLEYSOLIC | 0 | 0 | 0 | 0 | 0 | |
| 6 | 8 | OXBOW O.BLC | 47 | 32 | 21 | 3.2 | 0 | Loam |
| 7 | 7 | YORKTON O.BLC | 46 | 34 | 20 | 4 | 0 | Loam |

FIG. 4.5.

☑ Automatically generate water maps. As Company: [CropPro Consulting ▼]

Frequency of generation: [Every 4 Days ▼] Day of generation, if weekly: [Sunday ▼] Local hour of generation: [4 ▼] : [Min 30 ▼] * Note: Scheduling Details aren't updated until you synchronize with the server.

I suggest you create the map at 4:30AM every day. Scheduling maps when the sun has risen will affect the soil water balance because the model starts drying out the soil when the sun comes up, but at different rates if sunny/cloudy. The earliest sunup for this year is [4:36 AM] local time. You probably don't want to go earlier than this.

FIG. 4.6.

Static Field Properties:
Field Latitude, Longitude of the weather station in field: Latitude (-90 to 90): [52.456422] Longitude (-180 to 180): [-104.44551] View in: Google Maps Google Earth for Mac
... Or in Degrees,Minutes,Seconds, Latitude: [0] ° [0] M [0] s [0] , Longitude: [0] ° [0] M [0] s [0]  ☐ Input in DMS.
Primary Weather Data Source: [Pessl ▼]

Add a weather station:
Pessl Station Name: [UNKNOWN] Pessl Station ID: [ ] Station Key: [ ] (details located on silver sticker inside head unit) [Submit]

FIG. 4.7

Farming Season Start: 5/16/2021　　Farming Season End: 10/15/2021　　Refresh

Export to CSV: WaterMaps\WeatherCSV\2021-05-16 to 2021-10-15.csv　　Export

Selected Weather station name: 00208339, 2021 Smart Farm Wheat Zone 5 near (-104.44555, 52.406422)

Wind Weather data from: 00208339, 2021 Smart Farm Wheat Zone 5

RH Weather data from: 00208339, 2021 Smart Farm Wheat Zone 5

Solar Radiation Data Type: CALCULATED

Details:

| Time | High Temp degC | Low Temp degC | Humidity %RH | Precipitation mm | Solar Radiation w per m2 | Wind km per hr |
|---|---|---|---|---|---|---|
| May 16, 2021 12:00 AM | 12.79 | 12.79 | 61.17 | 0 | 0 | 14.9 |
| May 16, 2021 01:00 AM | 11.64 | 11.64 | 64.13 | 0 | 0 | 11 |
| May 16, 2021 02:00 AM | 11.18 | 11.18 | 68.08 | 0 | 0 | 9.8 |
| May 16, 2021 03:00 AM | 12.37 | 12.37 | 62.26 | 0 | 0 | 10.3 |
| May 16, 2021 04:00 AM | 12.25 | 12.25 | 60.33 | 0 | 0 | 13 |
| May 16, 2021 05:00 AM | 11.93 | 11.93 | 62.53 | 0 | 185.84 | 11.8 |
| May 16, 2021 06:00 AM | 12.88 | 12.88 | 57.66 | 0 | 226.73 | 13.7 |
| May 16, 2021 07:00 AM | 14.63 | 14.63 | 50.77 | 0 | 228.35 | 14.1 |

Figure 4.8

METHOD AND SYSTEM FOR CHARACTERISING THE SOIL MOISTURE CHARACTERISTICS OF MANAGEMENT ZONES IN BOTH TIME AND SPACE, SPECIFIC TO ZONE-BASED MANAGEMENT FOR VARIABLE RATE CROP INPUTS

PRIOR APPLICATION INFORMATION

The instant application claims the benefit of U.S. Provisional Patent Application 63/318,557, filed Mar. 10, 2022 and entitled "A METHOD AND SYSTEM FOR CHARACTERISING THE SOIL MOISTURE CHARACTERISTICS OF MANAGEMENT ZONES IN BOTH TIME AND SPACE, SPECIFIC TO ZONE-BASED MANAGEMENT FOR VARIABLE RATE CROP INPUTS", the entire contents of which are incorporated herein by reference for all purposes.

FIELD OF THE INVENTION

The present invention relates to methods and systems for in-season management of crop inputs such as fertilizer, seed, irrigation water, herbicides, and insecticides based on variable plant available soil moisture across agricultural fields throughout a growing season. The method considers soil, topography, and weather as variables across agricultural fields and outputs plant available soil moisture maps of fields throughout the growing season that are used to support management decisions, create variable rate prescriptions, and predict water driven yield potential by management zone.

BACKGROUND OF THE INVENTION

Agricultural viability and productivity are constantly under pressure to not only produce higher yield per unit area of land to remain economically viable, but also to do this by not increasing agriculture's impact on natural resources. Environmental stewardship is becoming of greater significance to the consumer. At the farm level, this means improving nutrient and water use efficiency in dryland and irrigated fields where variable soil, water, and topography characteristics are known to exist.

Variable rate technology, with an emphasis on non-time variable characteristics i.e. physical characteristics such as soil texture or location within the local topography (for example, top of hill or bottom of slope), have the ability to improve nutrient and water use efficiency. Non-time variable characteristics (e.g. soil texture), once mapped spatially to an appropriate level of precision, becomes a significant base off which a better understanding of dynamic variables (e.g. soil moisture, nutrient concentration, crop performance etc.) can be interpreted and managed.

Soil moisture characterisation, both spatially and temporally, has been in use in many forms for some time. Methods range from mobile sensor systems to point source such as in the case of soil moisture probes which monitor a specific location, through to field-based systems, which monitor moisture content through a mass balance approach, assuming uniform conditions across the entire field. In most cases, a combination of soil moisture probes and mass balance is applied. The success of probe-based systems is determined by how representative the probe placement is within a field, which is known to be variable, and secondly by the number of measurement points (probes). The higher the number of probes, the better the result, although a high density of probes can be very expensive, and the compromise usually results in fewer measured locations leading to greater room for error. Both methods account for inputs through irrigation or rainfall and losses by evapotranspiration.

An example of a remote sensing method of characterizing soil moisture is the IrriWatch™ irrigation management system. It leverages the Surface Energy Balance Algorithm for Land (SEBAL), which measures latent heat flux between land and the atmosphere. Their method calibrates heat flux and relates it to land surface temperature. Several derivatives have been produced, including leaf temperature, solar radiation, crop leaf size, photosynthetic activity, evapotranspiration, soil moisture and crop production estimates. Once these parameters are calculated, Irriwatch has developed a relationship between plant temperature and moisture use and associates these with soil moisture fluctuations.

Published Canadian Patent Application 2987761, assigned to South Country Equipment, teaches a method of forecasting crop yield for an agricultural field based on the plant-available water within a growing season. The method uses historical average precipitation for a region, percent of historical precipitation received in a growing season, and plant available water from a moisture probe located in a field average area of a field to forecast yield at the end of the growing season. This invention has been adopted by broad acre farmers in North America; however, the system does not address the soil moisture variability throughout a field. The system assumes the soil in the field is uniform in its capacity to hold water. The system has no ability to create a map of plant available water variability across a field.

US Patent Application number 2020/0292472, assigned to Skaha Remote Sensing Ltd., teaches a method of soil moisture detection by means of passive microwave radiometers. The method passes a microwave sensor over the agricultural field to measure site specific soil moisture. Consequently, the system is not able to produce soil moisture maps on-demand throughout the year. Furthermore, the depth of sensing into the soil will be variable and not able to be documented with this method given variances in soil texture and temperature.

There exist many handheld devices that give single point soil moisture measurements; however, these are not practical for providing a high-resolution map of soil moisture across a field throughout the season.

Technology developed by NASA called Soil Moisture Active Passive (SMAP) has been available since 2015. The system uses microwave technology to measure soil moisture in the top 5 cm of the field. The system is limited by a resolution of 9 km and therefor not useful for site specific agriculture.

Published US Patent Application No 2013/0231968 A1, licensed to Phantom Ag Ltd. teaches a method and system for identifying management zones for variable rate inputs wherein the zones are developed using soil, water, and topography base maps. The base maps are combined into various approaches as a zone map, and a final zone map called a SWAT Map is selected based on observed field characteristics.

As can be seen, several techniques exist that attempt to address the issue of spatial soil moisture variability. At the forefront are satellite-based techniques or yield mapping-based techniques. These techniques attempt to map spatial variability by focusing on plant indices or yield response. Such an approach runs the risk of being reactive rather than proactive and can fail due to the following assumptions:

Yield is not always a good reflection of soil moisture status. It does not differentiate between too much or too little moisture e.g. soils that can hold less moisture may perform better in dry years than those that can hold more moisture. A plant's response to stress due to too much moisture or too little moisture is generally the same, and both responses can have an impact on yield. That is, as the spatial variability of yield mapping is not always consistent, cause and effect must still be determined.

Aerial (drone) or satellite-based solutions monitor crop condition by means of several crop indices. These indices reflect crop condition, which is prone to similar shortfalls as yield mapping i.e. cause and effect. Poor crop production, whether that is yield, vegetation index or biomass, does not clarify the reason for the good or bad yield.

Irrigation design and layout strategies are often limited by the number of soil samples taken during and used for design purposes. Although grid sampling and soil classification techniques help to define soil variability more precisely, decisions regarding where to sample or where to place a soil pit are still governed by a random grid sampling method.

Site or location specific tools such as soil moisture probes often suffer from poor distribution of monitoring points and therefore only reflect soil moisture in a single location i.e., they are point specific. The assumption is that the probe reflects the average soil moisture conditions for the entire field. These field average assumptions drive irrigation demand, fertiliser practices, crop stress management, and herbicide and pest management practices which run the risk of treating the entire field with a uniform application even though soil moisture conditions are known to vary within a given field. This potentially results in over or under application. The cost of increasing the number of soil moisture sampling points is often a disincentive as it becomes overly expensive and labor intensive to install and remove the probes.

Irrigation and drainage design often leverage composite or individual point specific sampling techniques during the design process. The lack of an understanding of spatial variability often results in designing for the average rather than optimising design specific to zones of uniform potential. Proactive irrigation designers are looking for methods to support variable rate or precision irrigation techniques. As such, a solution that is capable of driving precision irrigation and drainage techniques is needed.

These differences could be overcome by the measurement of and defining of zones through the capture of non-dynamic variables i.e. basing temporal forecasts such as crop yield or soil moisture content, on non-variable inputs such as soil texture. This produces maps from which the source of the variability cannot be due to the data used to produce the maps themselves. With regards to variable rate technology, this would provide a non-dynamic solution from which variable characteristics such as crop yield, can be assessed, such as, for example, do water collecting areas produce higher or lower yields, and what volume of water lead to higher or lower yield production.

As such, a targeted soil sampling process would provide a far higher degree of precision for example by defining the extent of areas requiring a particular irrigation method or strategy. Such a method would complement and guide the process of placing soil moisture or crop health monitoring devices within a field, which previously would have been randomly placed.

SUMMARY OF THE INVENTION

According to an aspect of the invention, there is provided a method for determining probe placement location within an agricultural field comprising: providing a combined elevational and electrical conductivity map of the agricultural field; using said combined map, grouping regions of the agricultural field with at least one common hydrological characteristic, thereby defining a management map of the agricultural field comprising one or more zones of at least one common hydrological characteristic; using said management map, determining at least one location for probe placement, according to one or more of the following: a) a probe is placed at a location which represents a median soil condition for the field; b) a first probe is placed at a location which represents a driest part of the field and a second probe is placed at a location which represents a wettest part of the field; c) a probe is placed at a location which represents a median soil condition for a respective zone or group of zones.

According to another aspect of the invention, there is provided a method for determining soil moisture characteristics within an agricultural field comprising: providing a combined elevational and electrical conductivity map of the agricultural field; using said combined map, grouping regions of the agricultural field with at least one common hydrological characteristic, thereby defining a management map of the agricultural field comprising one or more zones of at least one common hydrological characteristic, said hydrological characteristic selected from the group consisting of: soil texture; gravel content; organic matter content; sand percentage; silt percentage; clay percentage; elevation; and electrical conductivity; using said management map, determining at least one location for moisture probe placement, according to one or more of the following: a) a moisture probe is placed at a location which represents a median soil condition for the field; b) a first moisture probe is placed at a location which represents a driest part of the field and a second moisture probe is placed at a location which represents a wettest part of the field; c) a moisture probe is placed at a location which represents a median soil condition for a respective zone or group of zones; d) a moisture probe is placed at a location representing a zone's or group of zones' average soil texture, salinity and/or organic matter content; and e) a probe is placed at a location representing field average soil texture, salinity and/or organic matter content; determining at least one soil characteristic of a soil column at each moisture probe location, said soil characteristic selected from the group consisting of: sand percentage, silt percentage, clay percentage, gravel content, organic matter content and salinity; using said management map, said at least one moisture probe and said at least one soil characteristic, mapping at least one soil moisture characteristic of the agricultural field.

According to an aspect of the invention, there is provided a process whereby a temporal or static grid (comprising of a matrix of pixels) is calculated to characterise one or more of the following:

a) hydrological characteristics of the soil, including for example but by no means limited to one or more of: texture (for example, sand, silt, and clay %); organic matter content; gravel content; soil salinity; electrical conductivity; elevation; topography; flow accumulation pathways; depressions and areas susceptible to temporal inundation from water; surface infiltration rate including crop interception; sub-surface infiltration; and saturated and un-saturated soil moisture characteristics; and b) volume of water in the soil at one or more of the following: gravitational water; saturation point; field capacity; capillary water; temporary wilting point or stress point; wilting point; hygroscopic water; total plant available water; and readily available water.

According to another aspect of the invention, there is provided a method for determining the distribution of hydrological characteristics and water volume within a field for both hydrological and volume based temporal or static grids.

According to another aspect of the invention, there is provided a process whereby the spatial and temporal characteristics associated with areas within a field that are prone to inundation are defined for both volume, spatial extent, and duration of inundation.

According to another aspect of the invention, there is provided a process whereby the spatial and temporal characteristics associated with the time until which a crop will start to experience stress is defined.

According to another aspect of the invention, there is provided a process to determine the optimal timing, rate, and placement of, but not limited to, one or more of the following agricultural inputs: nutrient e.g. fertiliser; seed; variety selection and sowing; herbicide; fungicide; pesticide; and irrigation.

According to another aspect of the invention, there is provided a process to inform and guide field layout, development, and crop establishment with regards to, but not limited to, one or more of the following: drainage; irrigation layout; variable rate irrigation design; variable rate irrigation management; precision irrigation; land forming; and maximising farmable hectares and optimising crop input requirements.

According to another aspect of the invention, there is provided a process to inform and guide environmental requirements with regards to, but not limited to, reducing the downstream impact of agricultural inputs as follows: nutrient losses to surface and subsurface (groundwater) water resources; optimise and target herbicide, pesticide and fungicide application rates; optimise field-based water requirements and limit pressure on the water resources by spatially defining soil moisture availability and demand; set irrigation targets and resource allocation limits; reducing over application of water; and optimise management practices by defining areas susceptible to poor production due to too little or too much water.

According to another aspect of the invention, there is provided a process whereby a soil may be characterised by a multi-depth analysis of sampled soil at defined intervals down to a rooting depth, for example, to a depth of about 1.2 m.

According to another aspect of the invention, there is provided a process whereby solar radiation may be derived for fields in which this value is missing using surrogate values.

According to another aspect of the invention, there is provided a process whereby flow characteristics of a field are determined using topological and physical soil flow properties.

According to another aspect of the invention, there is provided a process to determine optimal placement of a moisture sensor in a field using inputs as described above.

According to another aspect of the invention, there is provided a process which integrates real time soil moisture sensor data with modeled soil physical and hydrological processes as described above spatially at a 2 m pixel resolution and at depth down to 120 cm and/or at two or more, three or more or four or more separate depths reflecting the natural stratification and moisture characteristics of the soil column.

According to another aspect of the invention, there is provided a method for the capture and integration of field specific data, appropriate to characterise the static and dynamic soil moisture characteristics, and incorporation of the data as described herein.

According to another aspect of the invention, there is provided a method for determining crop rooting depth, canopy cover and associated moisture demand.

According to another aspect of the invention, there is provided a method for guiding crop selection based on the soil moisture content of the soil at the time of planting.

According to another aspect of the invention, there is provided a method for forecasting yield potential within a growing season for a selected crop growing at the field site.

According to another aspect of the invention, there is provided a method which integrates climate station data to estimate crop water demand.

According to another aspect of the invention, there is provided a method wherein the estimated end date of the growth season is determined by establishing crop parameters and soil moisture availability to forecast the number of days to maturity of the crop.

According to another aspect of the invention, there is provided a method which adjusts crop soil moisture demand based on soil salinity.

According to another aspect of the invention, there is provided a method of establishing a crop water use efficiency function which can be used to transform the total available moisture for a growth season to a forecast yield potential for a selected crop at a field site within a growth season, the total available moisture representing the sum of current precipitation received from the beginning of the growth season to a sample date and estimating the remaining precipitation from the sample date to the end of the growth season, and the current soil moisture within the field site.

According to another aspect of the invention, there is provided a method for detecting divergence between real-time soil moisture sensors and modeled zone-based soil moisture.

According to another aspect of the invention, there is provided a method for profiling supplementary soil moisture sources such as groundwater and associated plant available moisture from capillary rise.

According to another aspect of the invention, there is provided a method for estimating the volume of water contributing to groundwater recharge.

According to another aspect of the invention, there is provided a method for estimating the volume of water contributing to surface water via overland flow.

According to another aspect of the invention, there is provided a method for estimating the volume of water contributed to the soil profile from snow melt based on measured and estimated snow depth.

According to another aspect of the invention, there is provided a method for manually capturing field-based soil moisture data used to correlate solution results with that of actual field conditions.

According to another aspect of the invention, there is provided a method of sourcing and automating the integration of the following data and combining the data outputs to generate spatially and temporarily variable soil moisture and crop related maps: climate station data; soil, water, and topography maps; crop specific data; soil hydrology data; soil probe data; and remotely sensed data.

According to another aspect of the invention, there is provided a computer software system which manages the capture, storage and mathematical modeling and processing of one or more of the above-described aspects. In some embodiments, this software system includes a graphical interface, graphical display, and user interface appropriate for use in a multitude of device platforms from desktop through to mobile applications.

In some embodiments of the invention, one or more of the following inputs are used: geo-referenced field surveys; soil properties; soil sensors; in-field elevation data; remotely sensed elevation data; and remotely sensed satellite data.

BRIEF DESCRIPTION OF THE DRAWINGS

In the accompanying drawings, which illustrate an exemplary embodiment of the present invention:

FIG. 2.1 is a flowchart illustrating the generation of static soil moisture characteristics.

FIG. 2.2 is a flowchart illustrating the generation of dynamic soil moisture characteristics.

FIG. 2.3 is an illustration showing a zone map and the resulting static soil moisture maps at wilting and saturation point.

FIG. 2.4 is an illustration showing a zone map and the resulting dynamic soil moisture maps at two different dates within a growing season.

FIG. 3.1 is a flowchart illustrating the climate, crop, and hydrological process.

FIG. 3.2 is a flowchart illustrating the high-level process.

FIG. 4.1 is a screenshot of the user interface used for the selection of appropriate data.

FIG. 4.2 is a screenshot of the user interface which allows the user to produce a water map based on a range of rooting depth and soil depth inputs.

FIG. 4.3 shows soil physical characteristics for 10 zones, reflecting the 0 to 30 cm depth of a field.

FIG. 4.4 illustrates the user interface populated with the soil physical characteristics and the resulting soil moisture characteristics e.g., the bucket full or the bucket empty.

FIG. 4.5 provides an example of soils data for a field in Saskatchewan, extracted from the CANSIS National Soil Database and produced by Agriculture and Agri-Food Canada (AAFC).

FIG. 4.6 shows the user interface which allows the user to define the frequency and time of day when water maps are produced.

FIG. 4.7 illustrates assigning geographic location to the position of the probe such that the climate and or soil moisture data captured by the probe can be utilised by the invention.

FIG. 4.8 provides an example of weather data for a field in Saskatchewan, Canada.

DESCRIPTION OF THE PREFERRED EMBODIMENTS

Figure 1:
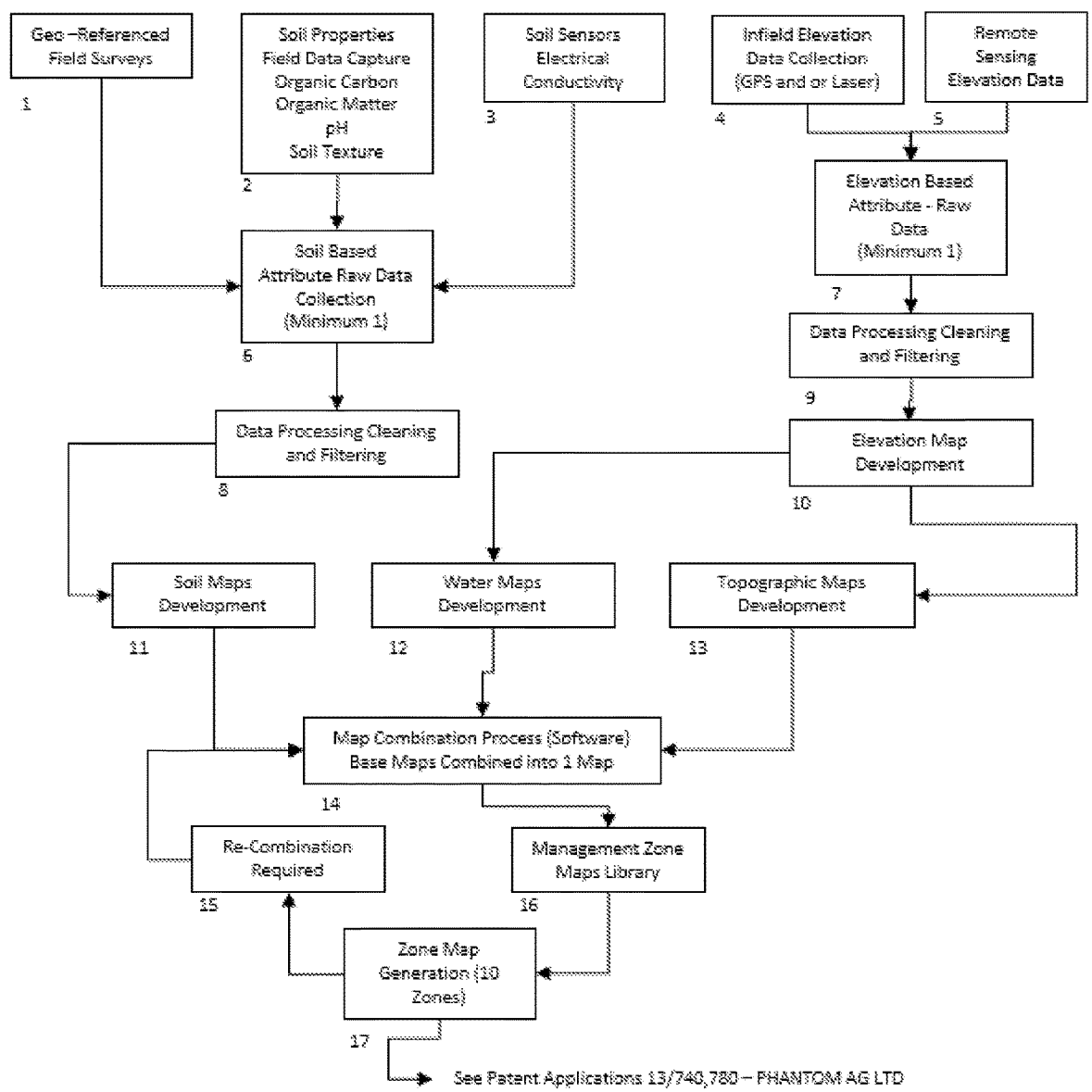
FIG. 1 is a flowchart illustrating a method for creation of a zone map based on soil, water, and topography factors (Described in Published US Patent Application 2013/0231968 A1).

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

In contrast with other spatial mapping solutions, described herein is a method for mapping the spatial variability of soil moisture through ground-based techniques which are proactive in defining and mapping soil moisture e.g. where am I likely to have dry areas that could be more susceptible to drought and how can I adjust my fertiliser or irrigation program to address this? This method reverses the logic of other available techniques e.g. imagery-based or yield-based solutions, which tend to be reactive by highlighting problems that have already occurred.

That is, an important distinction from other zone-based techniques such as biomass or crop observation techniques from satellite derivatives, is the grounding of the data through the measurement of and defining of zones through the capture of non-dynamic variables i.e. basing temporal forecasts such as crop yield or soil moisture content on non-variable inputs such as soil texture. In this way, the method is unique in producing maps from which the source of the variability cannot be due to the data used to produce the maps themselves. With regards to variable rate technology, this provides a solid non-dynamic solution from which variable characteristics such as crop yield can be assessed e.g. do water collecting areas produce higher or lower yields, and what volume of water leads to higher or lower yield production. The addition of the temporal soil moisture data is unique in defining spatial locations with uniform soil moisture conditions, thereby allowing relationships and recommendations regarding crop inputs such as fertiliser to be zone adjusted based on soil moisture variability. The method is unique in producing a digital dataset which refines not only dryland crop inputs but provides a suitable base for variable rate irrigation.

In some embodiments, there is provided a method and system for characterising soil moisture change over time (when and how much) and space (where) across agricultural fields. The method leverages soil, water, and topography data by the inclusion of zone-specific physical parameters. These parameters include, but are not limited to, soil texture and organic matter down to multiple depths, flow accumulation pathways, depressions, overland flow characteristics, and the integration of soil moisture probe and climate station data. The moisture characterisation process includes consideration for vadose zone hydrology by modeling the hydrological cycle including climatic, plant, surface, and subsurface moisture interactions. Consideration is included for the influence of groundwater on vadose zone hydrology. The resulting maps infer soil moisture variability spatially across the field and at multiple depths within the soil profile.

Accordingly, described herein is a method and system for a hydrological process that describes and characterises, either statically or temporally, soil moisture variability within agricultural fields, specific to zone-based field recommendations. Surface and subsurface hydrological processes are combined with soil physical properties, electrical conductivity (EC), topography, soil moisture sensors and climate parameters from weather stations, to produce a zone-based soil moisture balance. This process facilitates in-season optimization of crop inputs such as water from irrigation, seed, nutrients, herbicides, or pesticides based on the soil moisture conditions throughout a field.

In one embodiment of the invention, the method produces a map of relative properties, for example, electrical conductivity (EC) or EM38 capture data (which has a close relationship to EC and it can therefore be used as a proxy for EC) and topographical or elevation data. In some embodiments, the elevation data captured is actual, highly accurate elevation data (sub 2 cm). As will be appreciated by one of skill in the art, elevation provides an understanding of topography (depressions and hilltops), while EC provides a great understanding of sub-surface conditions. For example, areas with higher EC have a strong correlation with wet areas and/or areas with higher clay percentage or areas with higher salt levels or a combination of all three. Depressions are often wet because they store water, finer soil particles tend to be deposited there and as a result often have a higher clay content. In a single field, the depression with the highest EC does not necessarily have to have a high clay content but it is likely to be the wettest, saltiest and/or highest clay content in the field. As such, the maps are basically yield potential maps, wherein similar regions are grouped together, forming one or more zones, where each zone is defined by different yield limitations, for example, zones of soil that will behave the same to moisture. Generally, these have similar composition but not always. Two zones could have very different chemistry but very similar soil moisture characteristics.

For example, some fields have inverted soil characteristics i.e. clay soils at the top of a slope and sandy soils in the valley bottoms. While topography on its own would assume the inverse, soil moisture holding properties are a function of soil, not topography. Although topography influences it, the way in which a crop can access and utilise the soil moisture is governed by soil. Topography just tells you where water flows but not how it is stored in the soil medium and how long it will be stored, as discussed herein.

As discussed herein, this information is used to select position(s) for probes as well as for soil sample(s).

In some embodiments, the most representative location for the whole field is selected and one probe will be placed that best represents a single location that can be used to extrapolate characteristics for the rest of the field, that is, which represents a median soil moisture condition for the field.

In some embodiments, two probes are used for a monitoring program that focuses on the wettest and driest part of the field.

In other embodiments, the probe in a given zone is placed in a location that does not represent the wettest or the driest part of a zone.

While in some embodiments, three probes per field is optimal, the method can operate with a single probe and/or reference a probe from an adjacent field considered to be representative of the field of interest.

In some embodiments of the invention, texture is sampled at different depths, for example, between the surface and the projected rooting depths. This analysis provides soil physical properties (sand, silt, clay and organic matter) and chemical properties (macro and micro nutrients, ph., acid saturation, CEC and the like). For example, in some embodiments, sand %, silt %, clay %, organic matter % and salinity are used to characterise the soil moisture properties. For example, salinity and organic matter affect how easy it is for a crop to access soil moisture.

While soil texture analysis from a lab is recommended, as the sampling process or opening up of a soil pit gives a very good idea as to where there are changes (ground truthing), in some embodiments, nationally derived soil properties for different soil classes may be used.

For example, the soil may be sampled at one or more intervals down to a rooting depth for the intended crop, for example, 2 or more, 3 or more or 4 or more depths, for example at 0-30 cm, 30-60 cm, 60-90 cm, and 90-120 cm. As discussed herein, the key is that the sampling goes down as deep as, or just beyond the rooting depth of the crop. For example, potatoes may only be 60 cm.

As will be appreciated by one of skill in the art, the truthing process expands the agronomist's knowledge on the soil features because these features have been mapped in a relative way. Specifically, the mapping process tells you where to sample, the truthing process then tells you what the mapping process has captured spatially and characterises the soil properties using, for example, the texture analysis undertaken on the samples. Basically, this process brings a soil context to the map e.g., high clay content, actual nutrient that is causing the salt problem or the fact that the location may be saturated or wetter than the rest of the field. The truthing process identifies the spatial distribution of soil characteristics and identifies which feature in a field is yield limiting in each location i.e. is it salt, is it water or is it nutrient, as discussed above. For example, in one field, EC may be more dominant, in another field topography may be more dominant. The truthing process confirms this and firms up the agronomist's selection of a map.

In some embodiments, the probe(s) are moisture probes. In other embodiments, the probe(s) may also measure EC either directly or indirectly. As will be appreciated by one of skill in the art, this allows us to refine fertilizer applications based on nutrient flushes/EC spikes which effectively lose nutrient to the groundwater table.

As discussed herein, this information is used to provide a map of total available moisture and plant readily-available moisture. As will be appreciated by one of skill in the art, these measure different things. Total available water is the total volume of water available to a soil column, while plant available water is the volume that is available to the crop. Most crops can't extract water below wilting point, meaning that total available water includes that proportion of water below wilting point, whereas plant available water does not. Plant available water is the best measure to be used for irrigation purposes. Many soil monitoring sensors work off volumetric moisture content (VMC) as a percentage. VMC can be compared to total available water as both include the portion of water that is not plant available.

This spatial and temporal distribution of soil moisture within a field is what is mapped. The most important features are where is the field wet and dry and then secondly to quantify how much moisture is available. This is used to forecast for how many days the crop is going to be stress free. Finally, we are characterising the soil moisture characteristics down to 120 cm or rooting depth based on a 2 m pixel resolution. A soil moisture probe only provides an indication of soil moisture conditions for a single point whereas this method provides this for the entire field by 2 m pixel.

Stress in this context refers to the wilting point, which is dependent on the soil characteristics. For example, clay soils hold onto moisture much more tightly i.e. 15 bar pressure is achieved at much higher volume of water than a sand soil. In a clay, the wilting point could be at 30% Volumetric moisture content i.e. if you had 100 cm of soil, that would be equal to 30 cm or 300 mm of water in the soil column. A sandy soil on the other hand may hit 15 bar at 8% volumetric moisture content, or equal to 8 cm of water or 80 mm of water. Wilting point is the point at which the crop can no longer access the water stored in the soil column because it is held at too much pressure by the soil particles.

Most irrigation practices irrigate at when the profile reaches 60% of plant available water and the field is then irrigated up to 80% of the profile. With regards to fertilisation, as soon as the profile approaches wilting point, the crop is no longer able to extract nutrient from the soil matrix as nutrients travel into the crop via water. In general, any soil characteristics that affect a crop's access to water will affect nutrient uptake.

With regards to top-dressing, the question would be is there any point in applying additional nutrient if the crop is stressed in a particular location? As discussed herein, with this method, we can develop variable rate top-dress applications that account for this, for example, apply a basal application of fertilizer and then only top-dress those locations that will benefit from additional fertiliser.

According to an aspect of the invention, there is provided a method for determining probe placement location within an agricultural field comprising:

provide a combined elevational and electrical conductivity map of the agricultural field;

using said combined map, grouping regions of the agricultural field with at least one common hydrological characteristic, thereby defining a management map of the agricultural field comprising one or more zones of at least one common hydrological characteristic;

using said management map, determining at least one location for probe placement, according to one or more of the following:

a) a probe is placed at a location which represents a median soil condition for the field;

b) a first probe is placed at a location which represents a driest part of the field and a second probe is placed at a location which represents a wettest part of the field;

c) a probe is placed at a location which represents a median soil condition for a respective zone or group of zones.

The hydrological characteristic may be selected from the group consisting of: soil texture; gravel content; organic matter content; sand percentage; silt percentage; clay percentage; elevation; and electrical conductivity.

In some embodiments, the probe comprises a moisture probe and/or an electrical conductivity probe.

In some embodiments, the management map has a 2 m pixel resolution.

In some embodiments, a probe is placed at a location representing a zone or group of zones average soil texture, salinity and organic matter content.

In some embodiments, a probe is placed at a location representing field average soil texture, salinity and organic matter content.

In some embodiments, each probe is placed at a location most spatially representative of the zone being monitored.

A soil sample may be taken and analyzed at each location determined for probe placement.

The soil sample may be taken at two or more depths, for example, a surface sample and a rooting depth sample or, for example, samples at 0-30 cm, 30-60 cm, 60-90 cm and 90-120 cm.

The soil sample may be analyzed for at least one of the group consisting of: sand percentage, silt percentage, clay percentage, gravel content, organic matter content and salinity.

In some embodiments, the management map presents the agricultural field spatially at a 2 m resolution and at a depth of 120 cm.

According to another aspect of the invention, there is provided a method for determining soil moisture characteristics within an agricultural field comprising:

providing a combined elevational and electrical conductivity map of the agricultural field;

using said combined map, grouping regions of the agricultural field with at least one common hydrological characteristic, thereby defining a management map of the agricultural field comprising one or more zones of at least one common hydrological characteristic, said hydrological characteristic selected from the group consisting of: soil texture; gravel content; organic matter content; sand percentage; silt percentage; clay percentage; elevation; and electrical conductivity;

using said management map, determining at least one location for moisture probe placement, according to one or more of the following:

a) a moisture probe is placed at a location which represents a median soil condition for the field;

b) a first moisture probe is placed at a location which represents a driest part of the field and a second moisture probe is placed at a location which represents a wettest part of the field;

c) a moisture probe is placed at a location which represents a median soil condition for a respective zone or group of zones;

d) a moisture probe is placed at a location representing a zone or group of zones average soil texture, salinity and organic matter content; and e) a probe is placed at a location representing field average soil texture, salinity and organic matter content;

determining at least one soil characteristic of a soil column at each moisture probe location, said soil characteristic selected from the group consisting of: sand percentage, silt percentage, clay percentage, gravel content, organic matter content and salinity;

using said management map, said at least one moisture probe and said at least one soil characteristic, mapping at least one soil moisture characteristic of the agricultural field.

In some embodiments, each probe is placed at a location most spatially representative of the zone being monitored.

In some embodiments, said soil characteristic is determined from a soil sample, for example, a soil sample taken at two or more depths, such as a surface sample and a rooting depth sample.

In some embodiments, the soil sample comprises samples at 0-30 cm, 30-60 cm, 60-90 cm and 90-120 cm.

In some embodiments, the management map presents the at least one moisture characteristic of the agricultural field spatially at a 2 m resolution and at a depth of 120 cm.

In some embodiments, the at least one soil moisture characteristic is selected from the group consisting of: unsaturated soil moisture characteristics; saturated soil moisture characteristics; volume of water in a representative soil column; saturation point; wilting point; total plant available water; readily available water; soil water potential; upper soil moisture potential limit; and lower soil moisture potential limit.

In some embodiments, regions or zones of the agricultural field that are prone to inundation are mapped.

In some embodiments, readily available water is mapped.

In some embodiments, the readily available water map is used to project when a crop will experience water stress and/or to determine optimal timing, rate and placement of at least one agricultural input, wherein the at least one agricultural input is selected from the group consisting of: fertilizer; seed; herbicide; fungicide and irrigation.

In some embodiments, upper soil moisture potential limit and/or lower soil moisture potential limit is mapped. This may be used to guide field development and crop establishment, for example, one or more of: drainage; irrigation layout; variable rate irrigation design; variable rate irrigation management; precision irrigation; land forming; and maximizing farmable hectares and optimizing crop input requirements.

In some embodiments, flow characteristics of the agricultural field are mapped.

In some embodiments, static moisture characteristics are mapped.

In some embodiments, dynamic moisture characteristics are mapped.

In some embodiments, soil moisture content is mapped.

In some embodiments, the soil moisture content map is used to forecast yield potential within a growing season for a selected crop or to select a crop for planting in the agricultural field.

In some embodiments, the soil moisture content map is combined with climate station data to estimate future crop water demand.

As used herein, "mapping" in all of its grammatical forms, does not necessarily mean that a physical map, for example, a map that is a graphic representation of the field that is either printed and/or displayed, "mapping" also refers to assigning a specific value relating to for example current moisture content or moisture characteristics at a given location within the field, that is, within a soil column at a specific location within the field. Accordingly, in some embodiments, moisture characteristics of regions of the field such as for example but by no means limited to volume of water in a representative soil column; saturation point; wilting point; total plant available water; readily available water; soil water potential; upper soil moisture potential limit; and lower soil moisture potential limit are assigned values and these values are used to guide field development, for example, one or more of: drainage; irrigation layout; variable rate irrigation design; variable rate irrigation management; precision irrigation; and optimizing crop input requirements. For example, these assigned values may be uploaded directly to farm equipment, for example, irrigation equipment, so that resources can be applied preferentially to where they are needed most. As will be appreciated by one of skill in the art, in these embodiments, relevant field characteristics are still being "mapped", in that a dataset comprising values related to the moisture characteristics of sections of the field is created, that is, these values are "mapped" to locations within the field, which then may be used in a variety of ways, for example, for directing actions of farm equipment, without a traditional graphical map being generated or presented.

For example, in some embodiments, the map or dataset may be outputted as a prescription file based on either a. high resolution water map recommendation for nozzle specific control or b. pivot speed control so that our map is picking the most optimal rate for the width of the pivot based on the map. Other suitable uses for any one of the maps and/or datasets described herein for administering and/or regulating inputs will be readily apparent to one of skill in the art and are within the scope of the invention.

As discussed above, Published US Patent Application No 2013/0231968 A1 teaches a method and system for identifying management zones for variable rate inputs wherein the zones are developed using soil, water, and topography base maps. As discussed therein, these base maps are combined by various approaches into a zone map, and a final zone map called a SWAT Map is selected based on observed field characteristics. In some embodiments, particularly in the examples discussed below, the starting point for this invention is a SWAT Map which represents the static soil and topography characteristics of the field. The SWAT Map is designed to represent the plant soil moisture variability across a field in relative terms. This invention quantifies the plant available moisture within each SWAT Map management zone. However, a management zone map based on biomass or yield data is not sufficient for this invention. The zone map must be based on soil, water, and topography variables of a field for the method to be successful.

As such, in combination with soil moisture probes, typically placed in a zone 5 and ideally representing the field average soil texture, salinity and organic matter data, the maps produced provide a useful estimate of plant available water across a field. The soil, water and topography maps produced by the process described have been developed to include surface and sub-surface field hydrology. The result is management maps which depict relative soil moisture across a field. The method applies a desktop and field based "truthing" process to the maps produced. Field based "truthing" is guided by the production of a plurality of zone maps which are inclusive of the "truthing" process undertaken by the desktop exercise. During the process of "truthing", the optimal location for the placement of soil moisture probes is defined by the method. The method of soil moisture classification guides soil moisture probe placement by defining locations which are most spatially representative of firstly the zone being monitored, and secondly how probe measurement relates to the field at large. Unlike previous methods, this method uses non-temporal soil physical properties to characterise zones with uniform moisture characteristics. Unlike previous methods, this method applies a soil moisture balance, which is spatially represented and changes temporally in response to atmospheric conditions (e.g. rainfall, temperature, humidity etc.), plant soil moisture demand (evapotranspiration) and associated soil moisture storage and availability (ground and surface water stresses and losses). The in-season maps are used to develop variable rate irrigation and top dress fertilizer prescriptions. The maps are also used to identify areas of fields that are more prone to fungal or root borne disease in high moisture conditions and to predict water driven yield potential throughout the season.

As will be appreciated by one of skill in the art, the invention is further elucidated and/or explained by way of the following examples, particularly relating to the use of the SWAT maps; however, the invention is not necessarily limited to or by the examples. Accordingly, an exemplary method and system according to the present invention is set out below with reference to the accompanying figures.

Method

Soil Attributes. Referring to FIG. 1, the soil water and topography maps produced as described herein form the foundation for the exemplary method presented. Soil attributes are derived from the collection of soil-based data. In this example, this process involves the physical, in-field capture of soil samples by means of spiral auger or core sampling techniques, at various depths. The exemplary method described focuses specifically on the soil depth at which plant nutrition is most applicable i.e. the top 30 cm. The example presented here leverages the sampling done and samples at 0 to 30 cm, 30 to 60 cm, 60 to 90 cm, and 90 to 120 cm. As will be apparent to those of skill in the art and as discussed herein, in some embodiments, two or more depth samples, for example, 3 or more or 4 or more, or 5 or more are carried out. Furthermore, the depths and ranges of the individual samples may be varied, as discussed herein. Specifically, one key consideration is the rooting depth of the plant type that will be grown in the field, although additional factors are considered in some embodiments.

Referring to FIG. 2.1 and FIG. 2.2, the additional sampling includes the analyses of parameters specific to properties relevant to hydrological characterisation of the soil profile down to 120 cm, namely the static hydraulic properties 25 and dynamic hydraulic properties 37. Essentially, the exemplary method presented here leverages the spatial variability of the zone based field management system presented in FIG. 1, with the addition of the characterisation of soil variability associated with changes in soil moisture characteristics at depth i.e. 0 to 30 cm, 30 to 60 cm, 60 to 90 cm and 90 to 120 cm. Soil attributes could include, but are not limited to. texture, organic matter, organic carbon, pH, soil structure, erosion, salt levels, topsoil depth and soil moisture content. In this example, the soil attributes are captured at 4 depths to capture soil and moisture variability from topsoil through to subsoil horizons within the rooting zone.

Topography. Referring to FIG. 2.1 and FIG. 2.2, topography attributes are derived from the field-based collection of elevation data. In this example, field based data collection is undertaken by RTK GPS correction sufficient to produce a 2 m by 2 m pixel that reflects elevation change appropriate to derive hydrological characteristics relevant to inflows and outflows impacting the dynamic nature of soil moisture storage. These physical features include, but are not limited to, flow accumulation pathways, depressions, intra-field catchments and management interventions such as drains.

Water Attributes. Water attributes are derived from, but not limited to, a combination of topography, soil attributes, remotely sensed and soil moisture probe data. Water attributes include but are not limited to water sheds, flow accumulation pathways, water storage areas, water shedding areas, flow direction, aspect, slope, groundwater/surface water interaction, capillarity, infiltration rates, soil moisture storage capacity, crop canopy interactions and local climatic effects.

Soil, Water and Topography Relevance. Referring to FIG. 1, Phantom Ag LTD US 2013/0231968 A1 teaches a method and system for identifying management zones for variable-rate crop inputs, wherein the zones are developed using soil, water and topography base maps. The base maps are combined into various different zone maps, and a final zone map 17 is selected on the basis of observed field characteristics. In this example, this is the starting point for the SWAT water process, which as discussed herein, is one example of a map that may be used as a "starting point" for the invention. In this example, a zone map 17 is used as a base layer of information, although similar maps prepared with similar information may be used within the invention.

Soil Moisture Properties. Referring to FIG. 1, FIG. 2.1, and FIG. 3.1, soil properties 18, additional, but not limited to those captured for zone map generation 17 are included in characterisation of the soil profile 62 down to a depth approximating plant rooting depth. In this embodiment, soil characterisation divides the soil profile into four depths of 0 to 30 cm, 30 to 60 cm, 60 to 90 cm, and 90 to 120 cm. Attributes captured at each of the four depths include, but are not limited to sand/silt/clay percentage 20, gravel percentage 21, organic matter percentage 22, and salinity 23. These attributes form the minimum requirement to assign static soil properties 25 to Zone Maps 17.

Static Soil Moisture Properties. The methodology applied in the exemplary method for the static soil moisture properties follows that of Saxton & Rawls (2006) (https://doi.org/10.2136/sssaj2005.0117) in the Soil Science Society of America Journal titled Soil Water Characteristic Estimates by Texture and Organic Matter for Hydrologic Solutions in that for example the soil water characteristic equations are used to characterize the hydrology of soils across a field for this invention. This reference is accordingly hereby incorporated by reference for all purposes, particularly for these equations and the teachings associated therewith. For example, this method defines a soil's hydraulic property by estimating soil moisture characteristics using variables such as soil texture, organic matter, and structure. This method identifies a statistical correlation between these physical soil variables and a soil's water potential. Referring to FIG. 2.1, the method statistically identifies at different combinations of sand percentage, silt percentage, clay percentage 20, gravel percentage 21, organic matter 22 and salinity 23, the upper and lower soil moisture potential limits of a specific soil texture. This method is based on the volume of water extracted from a soil sample when placed under pressure i.e. 33 kPa to 1,500 kPa reflects Available Water 27 or the range at which water is available to plants. Above 1500 kPa and below 33 kPa, soil moisture is classified as Unavailable Water 26. The method predicts a range of static properties 25 for which those most relevant to the exemplary method described here are listed below:

Saturation 30. Soil saturation is the point at which a soil is unable to absorb any further moisture. The soil moisture is described as gravitational water 28 as the forces of gravity take effect and any water above field capacity 33 will drain through the forces of gravity.

Field Capacity 33. Field capacity is the point at which a maximum amount of water can be held by the soil column through the forces of soil adhesion and cohesion. In the same way as a meniscus can be observed in a glass of water, these forces are present between soil particles. The nature and arrangement of these particles determines the force that is required to remove moisture from the soil column. Field capacity has been applied by Saxton & Rawls (2006) to be at 33 kPa. This forms the upper limit of total available water 34, and is the point at which water can be extracted at very low pressures.

Wilting Point 31. This point represents a soil pressure of 1500 kPa, or very high pressure. Due to the high pressure with which soil moisture is bound within the soil matrix, wilting point reflects a volume of water that is considered unavailable to plants and is generally followed by severe plant stress.

Total Available Water 34. Total Available Water is the volume of water that plants can access. This is the volume of water between Field Capacity 33 and Wilting Point 31. Total Available Water is made up of Readily Available Water 35, which is the volume of water a plant can access without any stress. The balance of Total Available Water 34 can be accessed by plant, but the plant is likely to experience periods of temporary wilting such as during the hottest part of the day when plant water demand is highest.

Static soil properties 25 can be divided into unavailable soil moisture component 26 i.e. not-plant-available and the available soil moisture component 27 i.e. plant-available. Non-plant-available water comprises gravitational water 28, found in the profile at saturation 30, and hygroscopic water 29 found in the profile at or below wilting point 31. Available water 27 includes readily available water 35 (moisture that is easily accessed by the crop). Once readily available water 35 has been used, field capacity 33 and wilting point 31 form the upper and lower level between which total plant available water 34 is quantified.

Static Soil Moisture Maps Development. Referring to FIG. 2.1 and FIG. 3.1, static soil water maps (items 26 through to 35 are static maps, i.e. they do not change based on a change in soil wetness) that reflect the spatial distribution of unavailable water 26 and available water 27 form the foundation for the inclusion of temporal soil moisture variability in the form of dynamic soil moisture properties 37.

The exemplary method generates maps of Static Soil Moisture characteristics 25 through the process of characterising the soil profile at 4 depths. The method described by Saxton & Rawls (2006) is applied at the 4 depths and to each zone to assign upper and lower thresholds to the soil moisture balance described in the exemplary method. The management zones 10, derived from the SWATMAP now have zone-based soil moisture conditions, which have been derived from the soil sampling and analysis process. These soil moisture conditions in combination with the SWATMAP effectively map the volume of water that a particular location could hold as a maximum i.e. Saturation 30 and Field Capacity 33, or a minimum i.e. Wilting Point 31, and Available Water 27. The exemplary method provides the functionality to view this data based on the individual depths or alternatively based on the combination of all depths down to 120 cm.

Capillary Water 32. The inclusion of capillary water forms the first departure point from Saxton and Rawls (2006). The true definition of Capillary Water 32 is water held between the soil particles. It is defined here as the volume of water that is added to the soil profile through the process of capillarity. The exemplary method references the Food and Agricultural Organization of the United Nations, FAO (2018). This method presents a process which quantifies the volume of ground water that would move upwards through the soil profile by means of capillary action e.g. 3.5 mm/day. As will be appreciated by one of skill in the art, where shallow groundwater tables are present, Capillary Water 32 can contribute significantly to the soil moisture balance described by the exemplary method.

Assuming groundwater levels are static, the inclusion of Capillary Water 32 as a static variable holds true. For the most part, groundwater levels are dynamic, consequently, the contributions to soil moisture through groundwater are variable. In some embodiments, the exemplary method includes groundwater levels as an environmental variable. Shallow groundwater levels are measured by means of inspection tubes that are periodically measured manually or automatically by a groundwater probe. Water level fluctuations are included in the dynamic soil moisture characteristics and the associated calculation from which capillary action and the contribution of groundwater to crop evapotranspiration can be measured.

Dynamic Soil Moisture Properties. Referring to FIG. 2.2, dynamic soil moisture properties 37, for example, weather/climate 38, crop characteristics 42, environmental conditions 48 and management practices 56, all contribute to the variable nature of soil moisture and change in both spatial and temporal distribution. Rainfall 39 and evaporation 40 form the basis for climatic soil moisture inputs and outputs. Management practices 56, such as irrigation 57 and drainage 60, are management interventions introduced to account for a shortage or abundance of soil moisture. Environmental characteristics 48 govern the way in which moisture moves and/or is stored within the soil matrix. This includes soil moisture gains e.g., inflow 58 (infiltration from rainfall), capillary rise 49 from groundwater or a shallow water table and soil moisture losses through overland flow 51, deep percolation 52 (groundwater recharge) and evapotranspiration 44 (crop water use). Capillary rise 49 differs from capillary water 32 only in that capillary water describes the presence or absence of the influence of groundwater, while capillary rise 49 is the mechanism and volume of groundwater contributing to total available water 34. Soil moisture movement and storage is for the most part determined by topography 55, soil characteristics 62, and weather 38 and generally governs soil hydrology 54. Crop characteristics 42, such as crop type 45 and crop stage 46, place a moisture demand on the available soil moisture, resulting in evapotranspiration 44 which in turn is mediated by the spatial and temporal climatic 38, environmental 48 and management practices 56. To provide better clarification of the process, a raindrop falling on the soil surface either runs off or infiltrates the soil surface. Run-off, which is moisture that is lost to the field, is significantly influenced by topography and the nature of the soil surface i.e., is the soil bare or covered by vegetation. Once a raindrop has infiltrated the soil profile, the soil characteristics 62 tend to govern how it behaves below the soil surface i.e. is it held tightly to the soil particles, as would be the case in clay soils, or does it freely flow through the soil profile as it may in a sandy soil profile. The invention takes into account weather 38, crop characteristics 42, and environmental conditions 48 that affect soil moisture and combines all these factors and datasets into a climate model 41, crop model 47, soil hydrology model 54 and topography model 55 which then uses for example the SWATMAP 17 and soil moisture probes to model the soil moisture variability dynamically over time and space.

Dynamic Soil Moisture Maps Development. Referring to FIG. 2.2, the invention provides insight into the integration of Weather/Climate 38, Crop Characteristics 42, Environmental 48 and Management 56 variables.

The exemplary method begins with the process of defining Soil Properties 18. This process is a combination of Laboratory analysis 19a and In-Field analysis 19b. Laboratory Analysis 19a is the process of extracting physical soil samples at 4 depths, for example, at 0 to 30 cm, 30 to 60 cm, 60 to 90 cm and 90 to 120 cm for all zones or a subset of zones that is considered representative. Samples are analyzed for Sand percentage, Silt percentage, Clay percentage 20, Gravel 21 percentage, Organic Matter content 22 and Salinity 23. This process also defines the current soil moisture condition through In-Field Analysis 19b which, through installation of temporary soil moisture probes or Permanent Soil Moisture probes 67, and/or laboratory analysis 19a, determines a snapshot of the soil moisture condition through probe, hydrometer or gravimetric methods. The result is a "snapshot" of the most likely soil moisture condition on the day of sampling and reflects the point at which the Dynamic Properties 37 of the soil moisture balance are applied.

The exemplary method uses a combination of inputs to represent the change in the soil moisture conditions over time. Soil Moisture Probes 67 form the basis for validating modeled results from the exemplary solution. Moisture Probe 67 placement is guided by the Zone Map 17. In this example, zone maps 17 representing 10 zones with differing soil, topographic, crop types, static soil moisture, and dynamic soil moisture characteristics are connected to soil moisture probes 63. The Topography Model 55 generates several potential Permanent Probe 67 locations by identifying optimal locations within a zone for probe placement.

Soil moisture probes are optimally placed within a field by means of a statistical method that selects Optimal Moisture Probe Placement 63 locations that best reflect the size and distribution of zones within a field. In this example, the method applies the Topographic Model 55 and identifies saddles within a zone for probe placement, so as to ensure the probe placement does not represent the wettest or the driest part of a zone. If a single moisture probe 67 is to be placed in-field, the method identifies a zone 5 position which represents a median soil moisture condition for the field. If more probes are to be placed in-field, the method seeks additional locations that statistically represent for example a location between zones 1 and 5 and between zones 5 and 10, depending on the number of probes being placed. While in some embodiments, three probes per field is optimal, the method can operate with a single probe and/or reference a probe from an adjacent field considered to be representative.

Soil moisture probes 67, that provide data to the exemplary solution, are calibrated at all depths, for example, 0 cm to 30 cm, 30 cm to 60 cm, 60 cm to 90 cm, and 90 cm to 120 cm, to represent the hydrology of the soil texture 20 that the probe 67 is measuring. Soil characteristics 62, once populated with the soil texture 20, results in a solution that reflects probe calibrated and model calibrated soil moisture conditions. The solution consequently reflects both the characteristics of the matrix (i.e. texture 20, gravel 21, organic matter and salinity 23) and actual or instantaneous soil moisture conditions as reflected by soil moisture probe(s) 63.

Surface Hydrology Characterisation 64 is undertaken to ensure that the Soil Characterisation 62, which focuses primarily on sub-surface hydrology, considers overland flow pathways which contribute, store, or distribute water within the landscape. This process is a combination of desktop analysis through Remotely Sensed Data 64a and Surface Hydrology Features 64b generated by the Topography Model 55. The result is Recombination of Zone Maps 65 which best reflect the Static 25 and Dynamic 69 Soil Moisture Characteristics of the field.

In some embodiments, the method applies a Geographic Location 66 to connect the appropriate soil moisture probe 67, and/or Weather Station 68a connected to the in-field probe or closest weather station in a nearby field. Using spatial techniques, the process of selecting appropriate climate data firstly looks for a representative In Field Weather Station 68a. In the event an in-field weather station is not found or only has part of the data required for the climate model to run the software identifies the closest Regional Weather Station 68b, and uses this data to provide Weather data 38 to the climate model 41

In some embodiments, the method applies the Static Hydrological Characteristics 25 to generate a range of soil moisture conditions that reflect the hydrological characteristics of the zone. The exemplary method then applies the Dynamic Hydrological Characteristics 37, for example, how wet was the zone at the starting point, followed by how the zone changed over time relative to the upper threshold or Field Capacity 33 and the lower threshold or Wilting Point 31. The output may be, for example, hourly, daily, or weekly Soil Moisture Maps 69.

Crop Characteristics 42 and associated soil moisture demand can be variable due to crop type, global location and/or soil limitations that are not always identified by defining the Hydraulic Properties 24. The exemplary method addresses these limitations through the process of Soil Moisture Map Validation 70, which relies on the introduction of soil moisture probes 67 and remotely sensed data 70a. The exemplary method flags Divergence 71 associated with a probe and or remotely sensed data such as thermal imagery.

Divergence 71 with regards to Soil Moisture Probes 63 takes the form of identifying trends between the model and the probe to ensure all depths and all zones are responding in a similar way to the climatic conditions (moisture inputs and loss) experienced by the field. In this case, by default, the method applies crop factor 86 as part of the Crop Model 47, as recommended by the FAO (2018). In combination with the crop factor, the exemplary method calculates rooting depth 85 and associated crop moisture demand or loss from the soil column to the atmosphere via Evapotranspiration 44. At any point in the Crop Model 47, should the soil moisture probe suggest that a specific depth or a point specific Zone Map 17 location is on a daily basis using more or less moisture than the model and trends suggest that divergence is consistent and likely to result in drift between the exemplary solution and the probe(s), the exemplary method adjusts the factor applied to ensure consistency. For example, if the exemplary method is predicting 5 mm/day Evapotranspiration 44, but the probe is suggesting 3 mm/day, to avoid a consistent drift of 2 mm/day, which would result in an unrealistic soil moisture deficit, the exemplary method applies a factor so as to align modeled Evapotranspiration 44 with measured Evapotranspiration 41.

Secondary to Divergence 71 identified by soil moisture probes, remotely sensed data is used by the exemplary solution to identify areas within the field of active and in-active growth. The exemplary method recognises that Static Hydrological Characteristics 25 and Dynamic Hydrological Characteristics 37 differ between Mapped Zones 17 due to differences in surface and sub-surface hydrology. The addition of Remotely Sensed Data 72b provides the exemplary method with a mechanism to validate plant presence or absence across the field. Remotely Sensed Data can take several forms such as, for example, thermal imagery. Identifying crop presence or absence utilises a combination of Remotely Sensed data 72b sources and identifies areas with potentially lower or higher soil moisture demand relative to the Soil Moisture Probes 63. While Soil Moisture Probes 63 provide point specific calibration, the exemplary method utilizes thermal imagery to identify areas of active vs inactive growth. Areas with high temperature generally reflect locations where the crop is showing stress. Areas with low temperature will identify areas with maximum moisture demand. As such, Evapotranspiration 44 can be adjusted relative to maximum demand as calculated by the exemplary method and reduced demand as identified by locations showing moisture stress. Divergence 71 in the exemplary method is validated volumetrically through Probe Calibration 72a, and spatially through Remotely Sensed Data 72b.

A detailed diagram of the Soil Moisture Map Generation Process 100 is illustrated in FIG. 3.2. This flowchart illustrates how the Climate Station 68, Zone Maps 17, Crop Model 42 and Hydrology Model 61 are combined in the process of generating Soil Moisture Maps 100. The exemplary method applies a combination of infield weather station 68a and regional weather station 68b data to provide data at an hourly timestep suitable to populate temperature 75, wind speed 76, relative humidity 77, solar radiation 78 and precipitation 79.

A primary product of Climate Station data 68 is the calculation of Potential Evapotranspiration (PET) 80 as defined by the FAO Irrigation and Drainage Research Paper 56—Crop Evapotranspiration—Guidelines for computing crop water requirements (2005), ISBN 92-5-104219-5, the entire contents of which are incorporated herein by reference for all purposes. The method leverages this research to determine crop evapotranspiration 83 and Adjusted Evapotranspiration 84. Crop stress is determined by the hydrology model 61 and is influenced by both Soil Salinity 23 and Dynamic Soil Moisture properties 37. The solution accounts for crop type 45, crop age 46, crop stage 46a, crop cover 43 and crop rooting depth 85 in the context of crop stress 87 and selects a crop factor 86 that is applied to Adjusted Crop Evapotranspiration (ETcadj) 84.

The exemplary method applies Climate Model 41, Crop Model 47, hydrology model 54, topography model 55 and Zone Maps 17 to produce Soil Moisture Maps 100 based on an hourly timestep. FIGS. 3.1 and FIG. 3.2. provide insight into an overview and detailed view of the data selection and recombination process to produce water maps 100. The generation of these maps considers soil moisture losses and gains relevant to both surface hydrology 88 and sub-surface hydrology 94 to represent a field's spatial and temporal soil moisture variability.

The soil moisture maps 100 are available for viewing within a mobile or desktop farm management software platform. The maps may be used to create in-season variable rate fertilizer prescriptions, indicate areas of fields more prone to fungal diseases, and plan inputs for the following year based on end of season moisture reserves.

Figure 4:
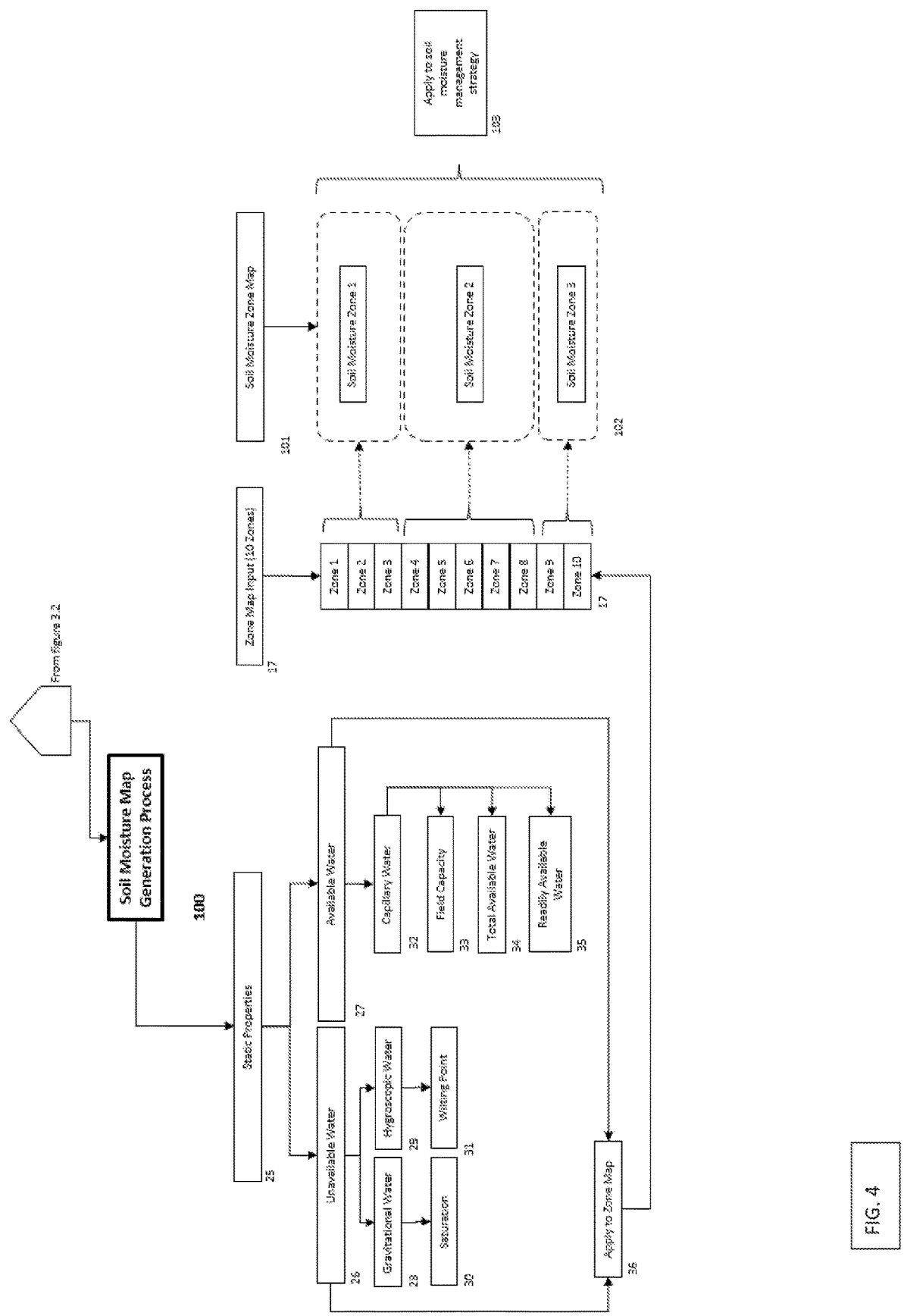
FIG. 4 is a flowchart illustrating the high-level process specific to developing a soil moisture management strategy.

Dynamic Soil Moisture Maps—the application of SWATWATER maps for irrigation scheduling. This embodiment of the invention, as described above, provides a foundation from which to map static and dynamic soil moisture characteristics. These datasets provide a platform from which to define zones with similar or uniform soil moisture characteristics/requirements. In the same way as the SWATMAPS process differentiates a field into zones with similar yield potential, the SWATWATER process described here provides a process for grouping zones one to ten into areas with similar soil moisture characteristics. The method is described as follows:

FIG. 3.2 has already described the process of capturing Soil Texture 20, Organic Matter 22, and Salinity data 23. The exemplary method identifies zones at four depths with similar static soil moisture characteristics i.e., as described in FIG. 2.1, Unavailable Water 26, and Available Water 27. Soil characteristics such as Saturation 30, Wilting Point 31, Field Capacity 33, Total Available Water 34, and Readily Available Water 35 are analysed by algorithms 102. These algorithms 102 isolate soil moisture trends with similar moisture management requirements and group these zones into soil moisture zones. The final step in the process is the application of the zones to a soil moisture management strategy 103. FIG. 4 illustrates the process described.

Overview of the Process Used to Create SWAT WATER Maps

User Interface

In some embodiments, the method is housed in a software package (SWAT Records) which serves to integrate the physical data e.g. soil texture, organic matter content etc. and the existing datasets e.g. SWAT Maps, elevation/topography datasets etc.

The process starts by ensuring the appropriate SWATMAP and elevation data set are loaded into the software. The exemplary process leverages the map selection process or ground truthing process, which combines physical in-field inspection of field characteristics with several algorithms to select a SWATMAPS which most accurately reflects the soil variability of the field in question. FIG. 4.1 shows a screenshot of one example of a user interface that may be used for the selection of appropriate data.

The software then provides the user with an option with regards to the water map they would like to produce. SWATWATER can produce water maps that reflect the total rooting depth—assumed to be 120 cm—or alternatively produce a map for the depth that the user would like to review, in this example, one of four depths namely: 0 to 30 cm, 30 cm to 60 cm, 60 cm to 90 cm or 90 cm to 120 cm. The user has the option to generate individual maps per depth or alternatively run an algorithm which combines all four depths into a single water map or run an algorithm which produces a map that depicts the soil moisture condition as rooting depth. FIG. 4.2 provides a screenshot of one example of a user interface which allows the user to produce a water map based on a range of rooting depth and soil depth inputs.

The rooting depth calculation applies crop characteristics such as crop type, age of crop or stage of crop and a specified planting date, to model the depth at which the crop is likely to be extracting moisture. In a real field situation, a crop can only access moisture that is within reach of its rooting bodies. A larger plant, with deeper roots is going to extract a greater volume of water, while conversely a younger plant with shallower roots and a smaller leaf area will have a lower soil moisture demand and the maps generated reflect this.

In this example, to understand the physical characteristics of the soil down to 120 cm, soil texture data, organic matter, salinity, and soil density data is captured for all 10 zones as per the SWATMAP selected and for each depth sampled (i.e., 4 depths). In this example, this data is gathered by using the soil sampling positions generated by the SWAT Records app and analysed in a soil testing laboratory. The results of this analysis are entered in into FIG. 4.3, which shows the soil physical characteristics for 10 zones, reflecting the 0 to 30 cm depth of a field. This process is repeated for all four depths to reflect the conditions down to 120 cm.

In this example, the data is analysed to generate soil moisture characteristics specific to each zone and each depth. The result is a dataset which quantifies the static soil moisture characteristics i.e., the volume of water that any location and/or depth could hold. In simple terms, if the soil is compared to a bucket—a bucket can only hold a certain volume of water, or it can be empty, or the volume of water would be somewhere in between full and empty. The static maps generated by the exemplary solution illustrate the bucket full and bucket empty. Specifically, FIG. 4.4 illustrates the user interface populated with the soil physical characteristics and the resulting soil moisture characteristics e.g., the bucket full or the bucket empty.

If a user decides not to take physical samples to populate the model with soil characteristics, the exemplary solution can be populated with research derived soil properties e.g. in the case of Canadian users, data is populated from the Agriculture and Agri-Food Canada (AAFC)-National Soil Database. An example of this is shown in FIG. 4.5, which is an example of soils data for a field in Saskatchewan, extracted from the CANSIS National Soil Database and produced by Agriculture and Agri-Food Canada (AAFC).

In this example, the user is provided with the option to automatically populate the physical data required for FIG. 4.3 or alternatively view and manually select the soil characteristics that the user believes are the most appropriate for the field, zone and soil depth being populated.

The final step in the process allows the user to generate static or dynamic maps of their choice e.g., Wilting point or bucket empty, Field capacity or bucket full etc. Should the user want to generate maps automatically, the exemplary method offers the user with an interface within which the user can select the frequency and time of day to generate water maps. One example of a user interface which allows the user to define the frequency and time of day when water maps are produced is illustrated in FIG. 4.6.

In some embodiments, soil moisture probe data is automatically provided by means of capturing the geographic location of the probe. In this embodiment, populating the Latitude and Longitude runs an algorithm which searches a probe within the network of probes connected and extracts the climate station data for the field in question. A secondary process runs in the background which interrogates the data to identify if there is any missing data required for the climate model to run. If data is missing, in this example, the closest regional climate station within the country of operation is identified and the data is patched with this information. An example of this is shown in FIG. 4.7 wherein the position of the probe is assigned a geographic location such that the climate and or soil moisture data captured by the probe can be utilised by the exemplary method.

The climate data is displayed in this example via a user interface. This display provides the user with details on the source of the data and also what data is sourced from what weather stations. One example of this is shown in FIG. 4.8, which is an example of weather data for a field in Saskatchewan, Canada. In this case, the user can clearly see that the data provided to the exemplary solution has been provided by the probe/weather station called Smart Farm Wheat Zone 5. This station does not provide Solar radiation data, as such you can see that Solar Radiation has been in this case calculated by the exemplary method.

In this example, the final datasets generated by the exemplary method are delivered to clients either via the desktop software or via the Crop Records App. In both cases, the data is delivered in several GIS and/or tabular or graphical formats. The data reflects both static and dynamic soil moisture conditions such that users-farmers, agronomists, consultants, and irrigation managers etc., can make precision agricultural decisions on fertility, crop establishment, land preparation, drainage and/or crop irrigation requirements.

The scope of the claims should not be limited by the preferred embodiments set forth in the examples but should be given the broadest interpretation consistent with the description as a whole.

The invention claimed is:

1. A method for determining probe placement location within an agricultural field comprising:
   providing a combined elevational and electrical conductivity map of the agricultural field;
   using said combined map, grouping regions of the agricultural field with at least one common hydrological characteristic, thereby defining a management map of the agricultural field comprising one or more zones of at least one common hydrological characteristic;
   using said management map, determining at least one location for probe placement, according to one or more of the following:
   a) a probe is placed at a location which represents a median soil condition for the field;
   b) a first probe is placed at a location which represents a driest part of the field and a second probe is placed at a location which represents a wettest part of the field;
   c) a probe is placed at a location which represents a median soil condition for a respective zone or group of zones.

2. The method according to claim 1 wherein the hydrological characteristic is selected from the group consisting of: soil texture; gravel content; organic matter content; sand percentage; silt percentage; clay percentage; elevation; and electrical conductivity.

3. The method according to claim 1 wherein the probe comprises a moisture probe or an electrical conductivity probe.

4. The method according to claim 1 wherein a probe is placed at a location representing a zone or group of zones average soil texture, salinity and organic matter content.

5. The method according to claim 1 wherein a probe is placed at a location representing field average soil texture, salinity and organic matter content.

6. The method according to claim 1 wherein each probe is placed at a location most spatially representative of the zone being monitored.

7. The method according to claim 1 wherein a soil sample is taken and analyzed at each location determined for probe placement.

8. The method according to claim 7 wherein the soil sample is taken at two or more depths.

9. The method according to claim 8 wherein the soil sample comprises a surface sample and a rooting depth sample.

10. The method according to claim 8 wherein the soil sample comprises samples at 0-30 cm, 30-60 cm, 60-90 cm and 90-120 cm.

11. The method according to claim 7 wherein the soil sample is analyzed for at least one of the group consisting of: sand percentage, silt percentage, clay percentage, gravel content, organic matter content and salinity.

12. The method according to claim 7 wherein the management map presents the agricultural field spatially at a 2 m resolution and at a depth of 120 cm.

13. A method for determining soil moisture characteristics within an agricultural field comprising:
    providing a combined elevational and electrical conductivity map of the agricultural field;
    using said combined map, grouping regions of the agricultural field with at least one common hydrological characteristic, thereby defining a management map of the agricultural field comprising one or more zones of at least one common hydrological characteristic, said hydrological characteristic selected from the group consisting of: soil texture; gravel content; organic matter content; sand percentage; silt percentage; clay percentage; elevation; and electrical conductivity;
    using said management map, determining at least one location for moisture probe placement, according to one or more of the following:
    a) a moisture probe is placed at a location which represents a median soil condition for the field;
    b) a first moisture probe is placed at a location which represents a driest part of the field and a second moisture probe is placed at a location which represents a wettest part of the field;
    c) a moisture probe is placed at a location which represents a median soil condition for a respective zone or group of zones;
    d) a moisture probe is placed at a location representing a zone or group of zones average soil texture, salinity and organic matter content; and e) a probe is placed at a location representing field average soil texture, salinity and organic matter content;

determining at least one soil characteristic of a soil column at each moisture probe location, said soil characteristic selected from the group consisting of: sand percentage, silt percentage, clay percentage, gravel content, organic matter content and salinity;

using said management map, said at least one moisture probe and said at least one soil characteristic, mapping at least one soil moisture characteristic of the agricultural field.

14. The method according to claim 13 wherein each probe is placed at a location most spatially representative of the zone being monitored.

15. The method according to claim 13 wherein said soil characteristic is determined from a soil sample.

16. The method according to claim 15 wherein the soil sample is taken at two or more depths.

17. The method according to claim 16 wherein the soil sample comprises a surface sample and a rooting depth sample.

18. The method according to claim 16 wherein the soil sample comprises samples at 0-30 cm, 30-60 cm, 60-90 cm and 90-120 cm.

19. The method according to claim 13 wherein the management map presents the at least one moisture characteristic of the agricultural field spatially at a 2 m resolution and at a depth of 120 cm.

20. The method according to claim 13 wherein the at least one soil moisture characteristic is selected from the group consisting of: unsaturated soil moisture characteristics; saturated soil moisture characteristics; volume of water in a representative soil column; saturation point; wilting point; total plant available water; readily available water; soil water potential; upper soil moisture potential limit; and lower soil moisture potential limit.

* * * * *